Figure 1:
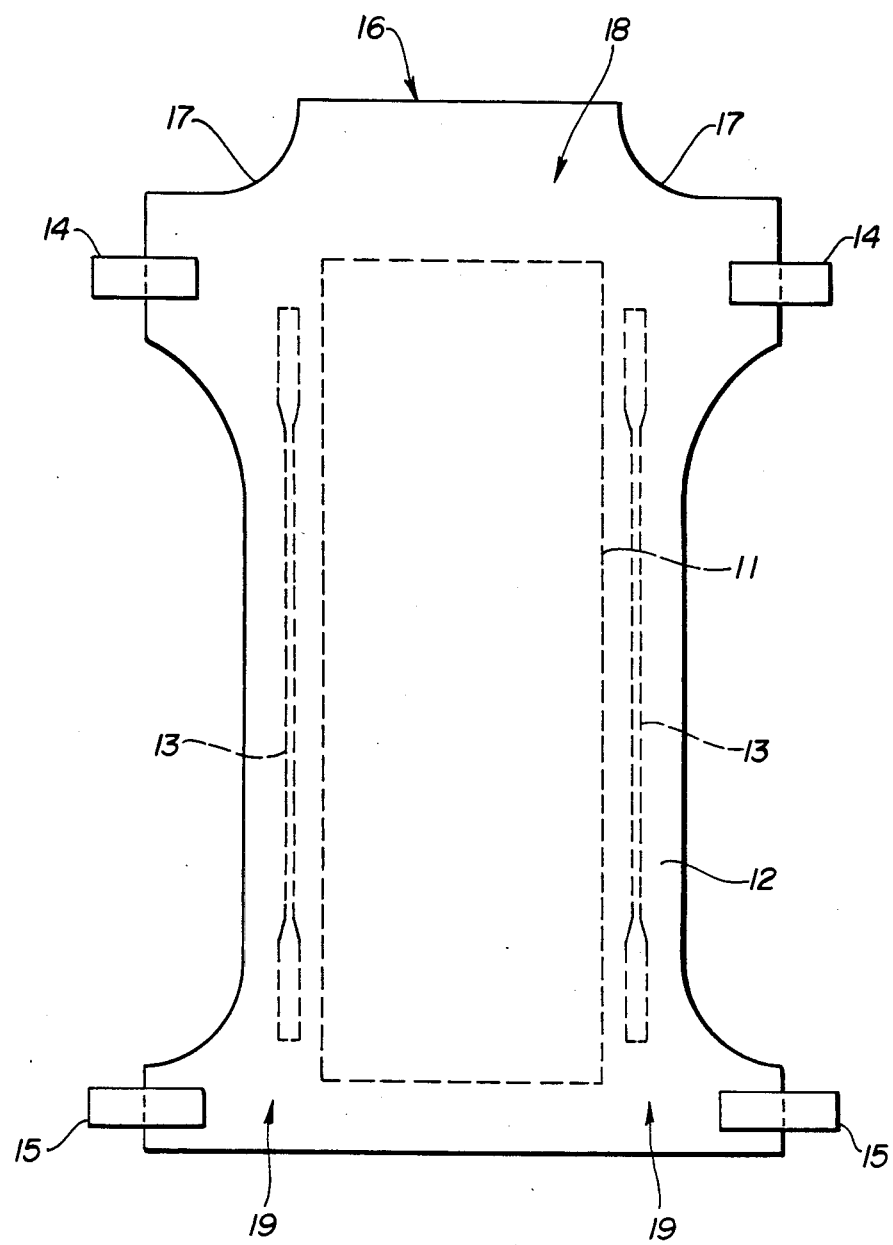

United States Patent [19]

Williams

[11] Patent Number: 4,753,650
[45] Date of Patent: Jun. 28, 1988

[54] DIAPER FASTENING

[75] Inventor: Frank C. Williams, Bradbury, Australia

[73] Assignee: Johnson & Johnson, New Brunswick, N.J.

[21] Appl. No.: 940,716

[22] Filed: Dec. 11, 1986

[30] Foreign Application Priority Data

Dec. 19, 1985 [AU] Australia .............. PH03952

[51] Int. Cl.⁴ .............................. A61F 13/16
[52] U.S. Cl. .................................. 604/389
[58] Field of Search ............ 604/389, 390, 385.1, 604/385.2, 386, 394, 399, 392; 128/78, DIG. 15

[56] References Cited

U.S. PATENT DOCUMENTS 3,598,114  8/1971  Lewis ........................ 128/78
3,610,244 10/1971  Jones, Sr. .................. 604/390
4,034,752  7/1977  Tritsch ...................... 604/390
4,037,602  7/1977  Hawthorne .................. 604/390
4,090,516  5/1978  Schaar ...................... 604/390
4,253,461  3/1981  Strickland et al. .......... 604/389

Primary Examiner—John D. Yasko
Attorney, Agent, or Firm—Lawrence D. Schuler

[57] ABSTRACT

The disclosure relates to a disposable diaper comprising an absorbent batt contained between a moisture permeable facing sheet and a moisture impermeable backing sheet, the diaper has front and rear portions and an intermediate crotch portion, first securing means for attaching the rear portion to the front portion of the diaper so as to hold the diaper on the user after the diaper has been positioned on the user, and second securing means for attaching the front portion to the rear portion of the diaper so as to improve the fit of the diaper around the waist region of the user.

8 Claims, 2 Drawing Sheets

DIAPER FASTENING

The present invention relates to disposable diapers and similar products such as incontinence pads.

Conventionally, disposable diapers comprise a liquid impermeable plastic backing sheet, a wood pulp absorbent batt and a moisture permeable facing sheet, the components being secured together by lines of adhesive with the backing and facing sheets usually directly adhesively interconnected around peripheral portions of the diaper. Some disposable diapers include elastic bands for providing a shaping and/or gathering effect for the diaper in the crotch region and facilitating the establishment of a fluid resistent seal around the infant's legs. Examples of known diapers are found in Australian Patent specification Nos. 526338 and 528786.

It would be desirable for a disposable diaper to be of a design which can be constructed very cheaply yet efficiently in a high speed manufacturing machine but also provide an excellent performance in effectively containing and retaining liquid discharges despite normal bodily movements. When an infant voids, a considerable volume of liquid is released at a localised region of the crotch portion of the diaper and this release is relatively fast thereby imposing considerable demands upon the performance of the absorbent material, which usually has a wicking effect to disperse the urine. Furthermore, in the case of a male baby, it is possible for the discharge of urine to be directed upwardly away from the crotch region and effective containment can often be a problem.

It is therefore desirable for a disposable diaper to be conformable to the shape of the baby in order to provide adequate containment, to have a good appearance, and to provide a high degree of comfort even after liquid discharge has taken place. There is a tendency for a diaper, when in use, to sag and not maintain a good fit around the baby's waist. Conventionally only the rear corner waistband portions of the diaper are secured to the front portion of the diaper by an adhesive tape located at each of these corner portions during the manufacturing process. When the diaper is applied to the infant, the tapes and associated portions of the rear waistband portion are drawn around the baby's waist and secured to respective sides of the front portion of the diaper either in the waistband region or elsewhere on the front portion. This tends to pull the rear waistband portion taut but leaves the front waistband portion without any significant tension applied thereto. As the diaper becomes loaded with fluid from the baby, the weight of such fluid, together with any internal collapse of the diaper structure, tends to create a downward drag, accentuating any previous sag or causing the diaper to sag if it otherwise fits reasonably well.

Apart from the obvious lack of good appearance arising therefrom, sagging also tends to allow the diaper to become so loose as to even fall away from the baby's body, particularly if no other containing garments are worn by the baby. Such sag, even if it does not lead to such a drastic result, may provide an opening whereby containment of the fluids is reduced.

Attempts have been made to reduce such poor fit and waist leakage and the problem has been addressed in various patent applications wherein the means to provide improved fit around the waist has been achieved with the use of elastic members in the waistband region. Use of elastic in the waistband region however, is a relatively expensive solution to the problem since the elastic needs to be laid across the diaper. Conventional machinery for manufacturing diapers produces diapers in an end to end fashion at high speed and therefore laying the elastic at right angles to the machine manufacturing direction requires a relatively more complex engineering process and has the potential to lead to higher consequent downtime. In addition, the elastic itself is a relatively expensive component of the product.

In addition, the conventional arrangement of a single pair of tapes, which in use become positioned at the front of the diaper, provide easy access for the baby's hands so that, particularly in the case of toddlers, it is possible for a baby to undo the tapes and to remove prematurely the diaper, especially if no other retaining or covering garment is worn.

The present invention is directed to a new and useful alternative to previous proposals.

According to the present invention there is provided a disposable diaper comprising an absorbent batt contained between a moisture permeable facing sheet and a moisture impermeable backing sheet, said diaper having front and rear portions and an intermediate crotch portion, first securing means for attaching the rear portion to the front portion of the diaper so as to hold the diaper on the user after the diaper has been positioned on the user, and second securing means for attaching the front portion to the rear portion of the diaper so as to improve the fit of the diaper around the waist region of the user.

Preferably, the first securing means comprises adhesive tapes consisting of a tape element adhesively secured to a respective side edge portion of the rear portion of the diaper, and adapted to form an adhesive connection with a convenient portion of the exterior of the backing sheet in the front portion.

Furthermore, with advantage the second securing means may comprise adhesive tapes consisting of a tape element adhesively secured to respective side edge portions of the front portion of the diaper, and adapted to form an adhesive connection with a convenient portion of the exterior of the backing sheet in the rear portion.

A preferred and important embodiment of the invention comprises a diaper wherein the front and rear portions have respective waistband portions, the tapes associated with the front portion being adhesively secured to respective side edge portions of the front waistband portion, and the rear waistband portion is shaped and dimensioned such that the side edge portions of the front waistband portion overlap the rear waistband to allow the second securing means to attach adhesively the front waistband side edge portions to the rear waistband portion when in use.

Figure 2:
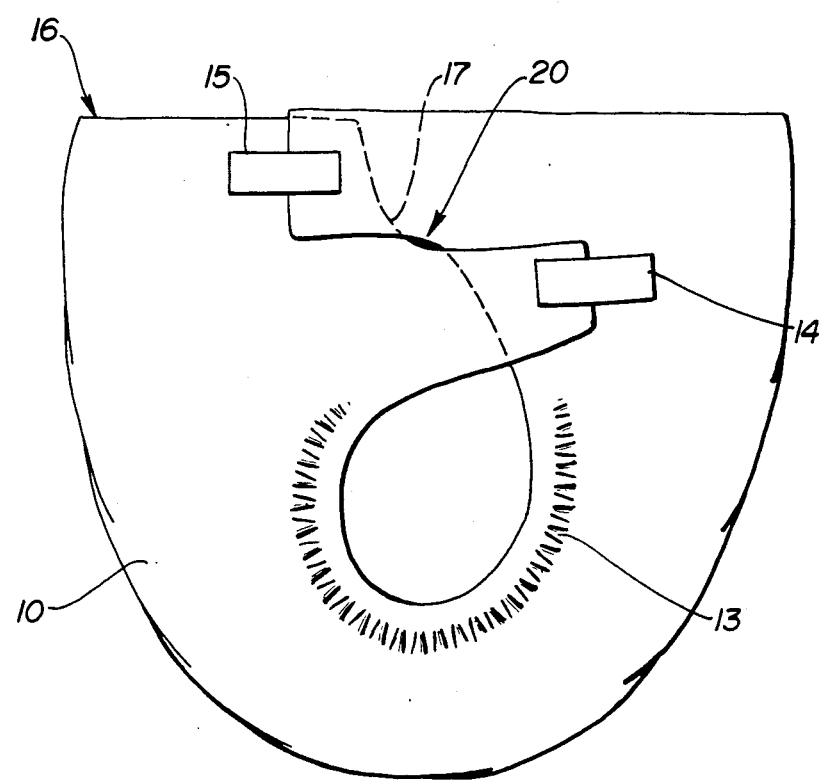

For illustrative purposes only an embodiment of the invention will now be described with reference to the accompanying drawings of which:

FIG. 1 is a plan view of a diaper in a stretched out configuration and embodying the invention; and FIG. 2 is a sketch of the diaper of FIG. 1 in the use configuration.

The diaper shown in the drawings comprises a polyethylene plastic backing sheet 10, a rectangular absorbent batt 11, and a moisture permeable non-woven fibrous facing sheet 12, of the same dimensions as the backing sheet 10 and secured thereto directly around the periphery of the diaper by lines of hot-melt adhesive. The backing and facing sheets are shaped to provide a narrow crotch region. Elastic bands 13 are provided adjacent the sides of the crotch region and are adhesively secured to the structure for the purpose of gathering and shaping the diaper as well as providing for a liquid seal around the infant's thighs.

Adhesive tape units 14 are provided at the sides of the rear portion 18 of the diaper together with a second pair of adhesive tapes 15 provided at the side portions of the front waistband portions 19 of the diaper. Each tape unit consists of a Y-shaped tape arrangement in which the inner surfaces of the upper arms of the Y shape are adhesively secured to the front and rear surfaces of the diaper by means of pressure sensitive adhesive. The free end of the tape (which is the bottom leg of the Y shape) has pressure sensitive adhesive on the front surface thereof. This free end has a releasably covering strip which is conveniently the outer surface of the upper leg of the Y shape, this outer surface being positioned on the facing of the diaper, the free end of the tape being folded onto this releasable surface during manufacture and peeled away from it when the diaper is to be used.

The rear waistband portion 16 is provided with a pair of cutouts 17 to allow the adhesive attachment of the front tapes 15 to the rear waistband portion as discussed below.

FIG. 2 shows the diaper in use. The rear tape 14 is attached to the front portion of the diaper in a conventional manner and then tape 15 on the front waistband portion is secured to the rear waistband portion 16. This is made possible by the provision of cutout 17 which allows the front tape and adjacent front waistband portion to overlap the rear waistband 16. The diagram is schematic in order to illustrate the overlap. In practice when tape 15 is properly pulled over and secured to the rear waistband 16, thereby providing adequate tension to the front waistband portion, there is no gap between the overlapping portions at 20. It will thus be observed that the cutout 17 in fact provides a shoulder in the vicinity of 20 over which the front waistband portion is tensioned. Such tensioning provides the beneficial effect of also tensioning the leg seal by effectively completing what is otherwise an open ended tensioning effect in a conventional diaper having a rear tape only.

The diaper of the present invention provides a better fit around the legs of the baby and more effectively prevents leakage. This can be appreciated from FIG. 2 where it can be seen that the leg openings of the present diaper are much more nearly round than the leg openings of prior art diapers. The leg openings in prior art diapers are characterized by a "tear-drop" shape and were more prone to leakage.

The claims defining the invention are as follows.

I claim:

1. A disposable diaper comprising an absorbent batt contained between a moisture permeable facing sheet and a moisture impermeable backing sheet, said diaper having first and second end portions, one of which is a front portion and one of which is a rear portion in use, and an intermediate crotch portion, said first end portion comprising first securing means for attaching said first end portion to the outer surface of the backing sheet at the second end portion of the diaper so as to hold the diaper on the user after the diaper has been positioned on the user, and said second end portion comprising second securing means for attaching said second end portion to the outer surface of the backing sheet at the first end portion of the diaper so as to improve the fit of the diaper around the waist region of the user.

2. A disposable diaper as in claim 1 wherein the first securing means comprises adhesive tapes consisting of a tape element adhesively secured to respective side edge portions of the first end portion of the diaper.

3. A disposable diaper as claimed in claim 1 wherein the second securing means comprises adhesive tapes consisting of a tape element adhesively secured to respective side edge portions of the second end portion of the diaper.

4. A disposable diaper as claimed in claim 1 wherein the end portions have respective waistband portions, the second securing means associated with the second end portion are adhesively secured to respective side edge portions of the second waistband portion, and the first waistband portion is shaped and dimensioned such that the side edge portions of the second waistband portion overlap the first waistband portion to allow the second securing means to attach adhesively the second waistband side edge portions to the first waistband portion when in use.

5. A disposable diaper as claimed in claim 1 wherein the first securing means comprises adhesive tapes consisting of a tape element adhesively secured to respective side edge portions of the first end portion of the diaper and the second securing means comprises adhesive tapes consisting of a tape element adhesively secured to respective side edge portions of the second end portion of the diaper.

6. A disposable diaper having a generally rectangular shape in a stretched condition and comprising an absorbent batt contained between a moisture permeable facing sheet and a moisture impermeable backing sheet, said diaper having first and second end portions each of which has a respective waistband portion, one of said end portion being a front portion and the other of said end portions being a rear portion in use, and an intermediate crotch portion, said first end portion comprising first securing means for attaching said first end portion to the outer surface of the backing sheet at the second end portion of the diaper so as to hold the diaper on the user after the diaper has been positioned on the user, said second end portion comprising second securing means for attaching said second end portion to the outer surface of the backing sheet at the first end portion of the diaper so as to improve the fit of the diaper around the waist region of the user, said first securing means comprising adhesive tapes consisting of a tape element adhesively secured to respective side edge portions of the first end portion of the diaper, said second securing means comprising adhesive tapes consisting of a tape element adhesively secured to respective side edge portions of the second waistband portion, said end portions providing front and rear waistband edges, and the corners of the rectangular shape being cut away from the sides of the first waistband so that the side edge portions of the second waistband portion overlap the first waistband to allow the second securing means to attach adhesively the second waistband side edge portions to the first waistband portion when in use.

7. A disposable diaper as claimed in claim 6, wherein the diaper has a narrower crotch portion and elastic member adjacent the margins of the crotch portion for gathering the diaper in this region and providing a big seal.

8. A disposable diaper as claimed in claim 6, wherein each of said cut aways has a smooth, curved concave edge for providing a shoulder over which a corresponding portion of the front portion of the diaper may slide during securement of the diaper to an infant.

* * * * *